US005665387A

United States Patent [19]

Mathieu et al.

[11] Patent Number: 5,665,387
[45] Date of Patent: Sep. 9, 1997

[54] METHODS AND COMPOSITIONS FOR PRIMARY AND SECONDARY PREVENTION OF AUTOIMMUNE DIABETES

[75] Inventors: Chantal Mathieu, Buizingen; Mark Waer, Heverlee; Roger Bouillon, Herent, all of Belgium

[73] Assignee: K.U. Leuven Research & Development, Belgium

[21] Appl. No.: 299,936

[22] Filed: Sep. 1, 1994

[51] Int. Cl.$^6$ .................................. A61K 9/20
[52] U.S. Cl. .................. 424/464; 424/455; 424/457; 424/458; 424/489
[58] Field of Search ................ 424/464, 455, 424/489, 457, 458; 514/460, 167

[56] References Cited

U.S. PATENT DOCUMENTS 5,298,525  3/1994  Yoon et al. ............... 514/460
5,321,009  6/1994  Baeder et al. ............. 514/4
5,342,625  8/1994  Hauer et al. ............... 424/455
5,401,731  3/1995  Calverley et al. .......... 514/167

*Primary Examiner*—Thurman K. Page
*Assistant Examiner*—William E. Benston, Jr.
*Attorney, Agent, or Firm*—Webb Ziesenheim Bruening Logsdon Orkin & Hanson, P.C.

[57] ABSTRACT

A method for modulating the immune system by administering one or more vitamin D (analogues) to a subject in need of immune therapy, which method may (but need not) include simultaneous treatment with a second immune system modulating active agent. Preferably, the treatment method is used to induce primary or secondary prevention of type I diabetes in a subject susceptible to type I diabetes. Administration of the vitamin D (analogues) is enteral or parenteral.

19 Claims, 3 Drawing Sheets

METHODS AND COMPOSITIONS FOR PRIMARY AND SECONDARY PREVENTION OF AUTOIMMUNE DIABETES

FIELD OF THE INVENTION

The present invention relates to methods and compositions for the treatment of autoimmune diabetes.

BACKGROUND

Type I diabetes, juvenile diabetes or insulin-dependent diabetes mellitus is a disease that affects children and young adults. The clinical features of the disease are caused by an insufficiency in the body's own insulin production due to the (near) total destruction of the insulin production. It has been found that this type of diabetes is an autoimmune disease (cf. Castano, L. and G. S. Eisenbirth (1990) Type I diabetes: A chronic autoimmune disease of human, mouse and rat. Annu. Rev. Immunol. 8:647–679).

In the autoimmune destruction of the β cells all cells of the immune system play a more or less important role. The B lymphocytes produce autoantibodies, whereas the monocytes/macrophages are probably involved in the induction of autoimmunity as antigen presenting cells.

It is assumed that T lymphocytes play a major role as effector cells in the destruction reaction. Like most autoimmune diseases type I diabetes arises because the tolerance of the T cells towards the body's own tissue ("self") is lost. The loss of tolerance towards β cells will thus result in the destruction thereof and diabetes will arise.

Furthermore, T cells carry the autoimmune memory. This will inter alia present a problem in transplantation of β cells. As a result of the renewed contact between the T memory cells and the new cells he memory cells will be reactivated leading to a secondary destruction of the cells. This will eventually result in the recurrence of the original autoimmune disease.

SUMMARY OF THE INVENTION

It is an object of the present invention to provide methods and compositions for the primary and secondary prevention of autoimmune diabetes. It is a further object the invention to provide methods and compositions for retarding or blocking the rejection of transplanted β cells, or β cell containing tissues, like islets of Langerhans.

DETAILED DESCRIPTION OF THE INVENTION

Figure 1:
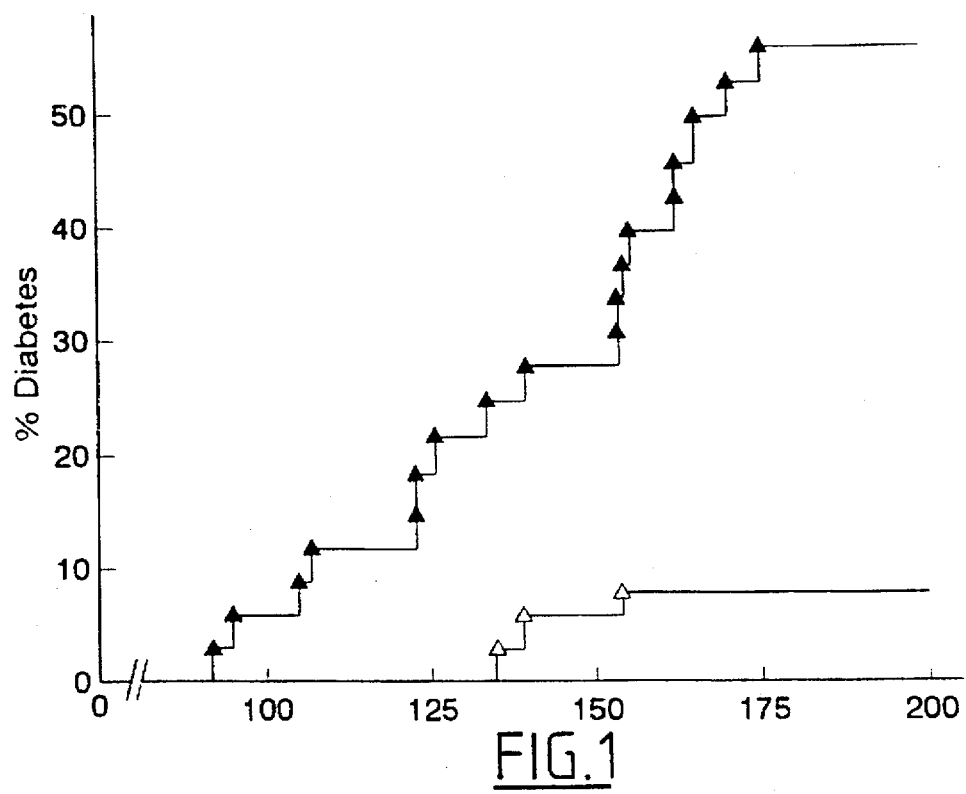
FIG. 1 shows the cumulative incidence of diabetes in female NOD mice.

In the research that lead to the present invention the NOD mouse has been used as animal model of the human disease. Convincing data have been provided to accept that juvenile or type I diabetes autoimmune disease that can he triggered by environmental favors in a genetically predispose individual. An imbalance between effector and reactor/suppressor immune cells eventually destroys the insulin producing cells and causes clinical diabetes.

Plain immunosuppression is indeed effective disease prevention in animal models, but less desirable in man because of important side effects. Recent interest is therefore focused on restoring the immune imbalance by upregulating the regulator/suppressor a of the system, preventing autoimmunity without impairing global immune defence systems.

1,25(OH)$_2$D$_3$, the active form of vitamin D, is such an immunomodulator. The present inventors we able to confirm this immune potential of 1,25(OH)$_2$D$_3$ in vivo as will be demonstrated in the examples, since 1,25(OH)$_2$D$_3$ was not only able to reduce the incidence of the histopathological lesion, insulitis, but also reduced the incidence of clinical diabetes in the spontaneously diabetic NOD mouse. Prevention of the autoimmune disease was accompanied by and most probably mediated through a restoration of regulator/suppressor cell activity in the normally suppressor-deficient NOD mice.

A possible obstacle preclinical application of this treatment with 1,25(OH)$_2$D$_3$ its effect on calcium and bone metabolism. Indeed long term treatment with the high doses of 1,25(OH)$_2$D$_3$ necessary to prevent the disease might cause mild hypercalcemia and bone decalcification.

Therefore it has been found according to a preferred embodiment of the invention that new structural analogues Of 1,25(OH)$_2$D$_3$ that have been synthesized previously, are 100 to 1000 times more active than 1,25(OH)$_2$D$_3$ in inducing cell differentiation or exerting immune effects, and are relatively less active in calcium and bone metabolism.

The invention thus relates to a method for treating primary autoimmune diabetes by administering a suitable dose of one or more vitamin D (analogue(s)) during a suitable period of time to a subject who has a predisposition to develop autoimmune diabetes. The vitamin D analogue(s) is/are administered in an amount to modulate the immune system in an animal or patient to which the amount is administered. A large number of other analogues of 1α,25 (OH)$_2$D$_3$ which display a dissociation of their potency to induce cell differentiation/immune effects and their calcemic effects in vivo, have a variable degree of similar protective effects and are able to induce primary or secondary prevention of type I diabetes. These analogues may be represented by the general formula

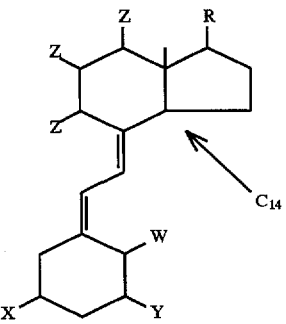

wherein x is H$_2$ or H(OH); Y is H(OH) or H(F); Z is H$_2$ or H-(alkyl) (C$_1$–C$_4$); W is H$_2$,=CH$_2$ or H(CH$_3$) and R is

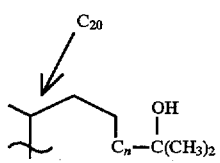

wherein one or more carbon atoms may be replaced by O or S and wherein n(3, or alkyl-, aryl-, alkenyl-, alkynyl-, fluoro-, thio-, cycloalkyl-, epoxy-, hydroxyl- or keto-containing derivatives thereof; and wherein $C_{14}$ and $C_{20}$ may be but need not be configured in the epi-orientation.

Examples of these compounds may be selected from but are not limited to the following list: $11\alpha$-vinyl-$1\alpha,25$-(OH)$_2D_3$, 22-dehydro-24,24,24-trihomo-$1\alpha,25$-(OH)$_2D_3$, 1F-25-(OH)-16-ene-23-yne-26,27-$F_6$-$D_3$, 1F-25-(OH)-16-ene-23-yne-$D_3$-26,27$d_6$, $1\alpha,24$(S)-(OH)$_2$-22-ene-26,27-cyclopropyl-$D_3$, 25,26-epoxy-23-yne-$1\alpha$-(OH)-$D_3$, $1\alpha,25$-(OH)$_2$-16-ene-23-yne-$D_3$-26,26,26,27,27,27-$d_6$, 1,25-(OH)$_2$-16-ene-23-yne-$D_3$, 22-oxa-$1\alpha,25$-(OH)$_2D_3$, 22-dehydro-24,24-dihomo-$1\alpha,25$-(OH)$_2D_3$, $1\alpha,25$-(OH)$_2$-24-dihomo-$D_3$, 24a,26a,27a-trihomo-22,24-22,24-diene-$1\alpha$, 25-(OH)$_2D_3$, $1\alpha,25$-(OH)$_2$-16-ene-23-yne-26,27$F_6$,-$D_3$, 20-epi-24-homo-$1\alpha,25$-(OH)$_2D_3$, 20-epi-24a,26a,27a-trihomo-$1\alpha,25$-(OH)$_2D_3$, 20-epi-22-oxa-24,24-dihomo-$1\alpha,25$-(OH)$_2D_3$, 20-epi-22oxa-24,24-dihomo-26,27-dihomo-$1\alpha25$-(OH)$_2D_3$, 20-epi-23-oxa-24a,24b-dihomo-$1\alpha,25$-(OH)$_2D_3$, $1\alpha$-F-25-(OH)-16-ene-23-yne-26,27-$F_6$-$D_3$, $\alpha$-F-25-(OH)-16-ene-23-yne-$D_3$-26,26,26,27,27,27,-$d_6$, $1\alpha,25$-(OH)$_2$-22-ene-24,24,24,-trihomo-$D_3$, $1\alpha,24$(S)-(OH)$_2$-22-ene-26,27-dehydro-$F_3$, $1\alpha,25$-(OH)$_2$,22,23-dihydro-24-epi-$D_2$, $1\alpha,25$-(OH)$_2$-22-ene-$D_3$, 22(R)-$1\alpha,25$-(OH)$_2$-22,23-diene-$D_3$, $1\alpha,25$-(OH)$_2$-$11\alpha$-ethyl-$D_3$, 22(S)-$1\alpha,25$-(OH)$_2$-22,23diene-$D_3$, 22-dehydro-26-homo-$1\alpha,25$(R)-(OH)$_2D_3$, 25,26-epoxy-23-yne-$1\alpha$(OH)-$D_3$, $1\alpha,25$-(OH)$_2$-(OH)$_2$-26,27-dimethyl-$D_3$, $1\alpha,25$-(OH)$_2$-16,23-diene-$D_3$, $1\alpha,25$-(OH)$_2$-23-yne-$D_3$, $1\alpha,25$(R)-(OH)$_2$-26-$F_3$-$D_3$, $1\alpha,25$-(OH)$_2$-16-ene-23-yne-$D_3$-26,26,26,27,27,27,-$d_6$, $1\alpha,25$-(OH)$_2$-20-epi-22-oxa-$D_3$, $1\alpha$-F-25-(OH)-16-ene-23-yne-$D_3$, $1\alpha,25$(OH)$_2$-16-ene-$D_3$, $1\alpha,25$-(OH)$_2$-24,26,27-trihomo-$D_3$, $1\alpha,25$-(OH)$_2$-22-oxa-$D_3$, $1\alpha,24$(S)-(OH)$_2$-22-oxa-$D_3$, $1\alpha,25$-(OH)$_2$-22-oxa-26,27-dimethyl-$D_3$, $1\alpha,25$-(OH)$_2$-16-ene-23-yne-$D_3$, $1\alpha,25$-(OH)$_2$-$D_3$-22-dehydro-24-homo, $1\alpha,25$-(OH)$_2$-22-dehydro-24,24-dihomo-$D_3$, $1\alpha,25$-(OH)$_2$-$D_3$-22-dehydro-26homo, $1\alpha,25$-(OH)$_2$-24a-homo-$D_3$, $1\alpha,25$-(OH)$_2$-24-dihomo-$D_3$, 26,27-$F_6$-$1\alpha,24$-(OH)$_2D_3$, $1\alpha,25$-(OH)$_2$-24$F_2D_3$, 24,24-$F_2$-24-homo-$1\alpha,25$-(OH)$_2D_3$, $1\alpha,25$-(OH)$_2$-26-homo-$D_3$, 24-$F_2$-26,27-dimethyl-$1\alpha,25$-(OH)$_2$-$D_3$, 1-$\alpha$-(OH)-26,27diethyl-$D_3$, $1\alpha,25$-(OH)$_2$-26,27-$F_6$-$D_3$, $1\alpha,25$(OH)$_2$-22-oxa-24,26,27-trihomo-$D_3$, $1\alpha$-(OH)-25,26-epoxy-23-yne-20-epi-$D_3$, $1\alpha,25$-(OH)$_2$-20-epi-$D_3$, $1\alpha,24$ (S)-(OH)$_2$-22-oxa-26,27-dimethyl-$D_3$, $1\alpha,25$-(OH)$_2$-26,27-$F_6$-22-ene-$D_3$, $1\alpha,25$-(OH)$_2$-24a,26a,27a-trihomo-22,24,-diene-$D_3$, $1\alpha,25$-(OH)$_2$-16-ene-23-yne-26,27-$F_6$-$D_3$$1\alpha,25$-(OH)$_2$-20-epi-24-homo-$D_3$,$1\alpha,25$-(OH)$_2$-20-epi-24a,26a,27a-trihomo-$D_3$, $1\alpha,25$(OH)$_2$-20-epi-22-oxa-24,24-dihomo-$D_3$,$1\alpha,25$(OH)$_2$-20-epi-22-oxa-24,24-dihomo-26,27dihomo-$D_3$, $1\alpha,25$-(OH)$_2$-20-epi-23-oxa-24a,24-dihomo-$D_3$, 20-epi-$1\alpha$-oxa-24-homo-$1\alpha,25$-(OH)$_2D_3$, $1\alpha,25$-(OH)$_2$-20-epi-22-oxa-24a,26a,27a-trihomo-$D_3$.

In allogeneic transplantation of islets of Langerhans, whole pancreas or isolated cells β in autoimmune diabetes patients two different phenomena are responsible for destruction of the transplant, namely the allograft rejection encountered in all allogeneic transplantations on the one hand and the recurrence of autoimmune destruction of the β cells induced by the T memory cells on the other hand.

It has now been found that the recurrence of diabetes after islet transplantation is also prevented by vitamin D analogues.

the invention thus further relates to a method for preventing recurrent autoimmune diabetes by administering a suitable dose of one or more vitamin D (analogue(s)) during a suitable period of time to a subject who has undergone an islet or β cell transplantation.

Furthermore it has been found that some vitamin D analogues are able to retard the destruction of transplanted islets of Langerhans to the same extent as cyclosporin A, which is usually use as an immunosuppressant for preventing the rejection of the transplanted tissue. Moreover it was demonstrated that by using cyclosporin A and vitamin D (analogues) together, each in a subtherapeutical dose, even more potent effects on islet survival were found than could be obtained when using the highest tolerable doses separately. This strongly suggests a synergistic effect of both compounds. This also indicates that vitamin D (analogues) may be used as dose reducing agents for more conventional immunomodulators like cyclosporin A.

The invention therefore also relates to a method or preventing the destruction of islets of Langerhans on β cells after transplantation by administering during a suitable period of time to a transplantation patient a subtherapeutical dose of one or more vitamin D (analogue(s)) together with a subtherapeutical dose of another immunosuppressant, e.g. cyclosporin A.

Another aspect of the invention relates to compositions for both primary and secondary prevention of autoimmune diabetes. The compositions comprise a relatively high amount of vitamin D (analogue(s)) together with a suitable excipient. The amount of the vitamin D (analogue(s)) is preferably such that the dose administered is higher than the physiological dose, preferably 2 times higher, more preferably 5 times higher, most preferably 10 to 100 times higher.

The invention further relates to therapeutical compositions comprising a combination of one or more vitamin D (analogue(s)) and one or more immunosuppressants, together with a suitable excipient. The amount of both active ingredients in the composition may be such that a subtherapeutical dose of both ingredients is achieved.

The composition may be administered continuously, intermittently, i.e. every other day, or during a limited period of time.

Pharmaceutical compositions, comprising vitamin D and/or its analogue(s) as the active ingredient for preventing primary and secondary diabetes have the form of powders, suspensions, solutions, sprays, emulsions, unguents or creams and can he used for local application, intranasal, rectal, vaginal and also for oral or parenteral (intravenous intradermal, intramuscular, intrathecal etc.) administration. Such compositions can be prepared by combining (i.e. by mixing, dissolving etc.) the active compound(s) in the form of a free acid or salt with pharmaceutically acceptable excipients with neutral character (such as aquous or non-aquous solvents, stabilizers, emulsifiers, detergents, additives), and further if necessary colouring agents and flavouring agents. The concentration of the active ingredient in a pharmaceutical composition can vary between 0.001% and 100%, depending on the nature of the treatment and the method of administration. The dose of the active ingredient that is administered can further be varied between 0.1 µg and 1 mg per kg body-weight, preferably between 0.1 µg and 100 µg per kg body-weight.

In this application the term "vitamin D (analogue(s))" is used to indicate both vitamin D in its active form, 1,25(OH)$_2D_3$, as well as analogues thereof, which provide a similar treatment effect in both the primary and secondary onset of autoimmune diabetes and which may act as a dose reducing agent for conventional immune suppressants, like cyclosporin A and the like.

The above and other aspects of the present invention will be illustrated in the following examples, which are in no way intended to limit the invention.

EXAMPLE 1

Primary Treatment of Autoimmune Diabetes by 1, 25 Dihydroxy-Vitamin D3 (1,25(OH)$_2$D$_3$)

Animals

NOD mice that were originally obtained from Professor Wu (1990, Beijing, China) were bred in our animalium (Proefdierencentrum Leuven) and kept under conventional conditions. Animals were fed a low-calcium, vitamin D replete diet (0.2% calcium, 1% phosphate, 2000 U vitamin D/kg; Hope Farms, Woerden, The Netherlands.)

C3H and C57B1/6 mice were purchase from Charles River (Wiga, Sulzfeld, Germany). Diabetes incidence at the age of 200 days in stock mice at the time of the study was 57% in female and 22% in male mice. After the age of 200 days, the diabetes incidence in the colony was less than 0.5% In this study only female NOD mice were used.

Treatment Regimen 1,25(OH)$_2$D$_3$ (Hoffman Roche, Nutley, N.J., USA) as dissolved in arachis oil.

Animals were divided into two groups: test animals (n=40) receive 1,25(OH)$_2$D$_3$ (5 µg/kg) in 0.05 ml arachis oil intraperitoneally every other day, while the control group (n=40) received arachis oil (0.05 ml) only. Treatment was started at the age of 21 days and terminated at the age of 200 days or on the day of diabetes diagnosis.

Evaluation of Disease and Insulitis

Mice were weighed weekly and glucosuria was tested three times per week starting from the age of 70 days using Ketodiabur Stix (Boehringer Mannheim, Mannheim, Germany). Diabetes was diagnosed in mice having positive glucosuria and glycaemia above 13.8 mmol/l on two consecutive days. Glycaemia was measured on a Glucoscot II Glucometer (Menarini, Firenze, Italy).

At diabetes diagnosis or at 200 days of age, mice were killed by either inhalation and cervical dislocation (24 h after the final injection). Pancreases were removed, fixed in Bouin's solution, embedded in paraffin and serial sections of the whole pancreas were made. Sections were stained with hematoxylin cosine.

Insulitis was evaluated by two independent investigators. A mean of 3 islets per pancreas were screened and the level of lymphocytic infiltration in the islets were scored as described previously (Mathieu et al. (1992) Diabetes 41(11): 1491–1495). Briefly, the following scoring system was used:

0=no lymphocytes in or around the islets;

1=periductular infiltrate;

2=per-islet infiltrate;

3=intra-islet infiltrate;

4=intra-islet infiltrate associated with β-cell destruction.

The mean score for each pancreas was calculated by dividing the total score by the number of islets scored. Any degree of lymphocytic infiltration (>0) was scored as positive.

Treatment with 1,25(OH)$_2$D$_3$ succeeded in reducing insulitis incidence from 81% (26 of 32 mice) in the control group to 58% (21 of 36) mice in the treated group (p<0.05). Animals with as few as one pathological islet were considered to have insulitis.

Also, the severity of inflammation in the islets of treated mice (2.1±1.4) was less than in the control group (3.2±1.4; p<0.025). Treatment with 1,25(OH)$_2$D$_3$ not only reduced insulitis incidence, but more importantly also reduced the cumulative incidence of diabetes at the age of 200 days, from 56% (18 of 32 mice) in the group to 8% (3 of 36 mice) in the treated group (p<0.001). The three mice that developed diabetes despite treatment with 1,25(OH)$_2$D$_3$, did so later than the control animals.

The above results are illustrated in FIG. 1 which shows the cumulative incidence of diabetes in female NOD mice. ▲, 1,25(OH)$_2$D$_3$ group (n-36); Δ, arachis oil treated group (n=32). Statistical analysis was performed using chi-square test (p<0.001).

Suppressor Cell Assay

One hypothesis for the precise immune mechanism which leads to the destruction of the insulin-producing β cells in the pancreas is an impaired suppressor system. It is thought that the activity of vitamin D (analogue(s)) may be based on the restoration of the suppressor function.

Therefore, the capacity to generate suppressor cells in an autologous MLR (Mixed Lymphocyte Reaction) was tested as described previously (Serreze & Leiter (1988) J. Immunol. 140(11):3801–3807). Briefly, T cells ($5 \times 10^6$/ml; $5 \times 10^5$ per well) from the test animal, enriched from splenocytes by nylon wool passage, were co-cultured with $^{60}$Co irradiated (3000 Rad) splenic leucocytes from the same animal ($5 \times 10^6$/ml; $5 \times 10^5$ per well) in RPMI 1640 medium supplemented with 10% fetal calf serum, glutamine, 100 U/ml penicillin, 100 µg/ml streptomycin and 0.2% mercaptoethanol in triplicate in flat-bottomed 96-well microtitre plates. Concurrently, bulk cultures consisting of $5 \times 10^6$ test responder T cells and $5 \times 10^6$ test stimulator splenocytes were established in upright 25-cm$^2$ culture flasks. On day 6 [methyl-3H]thymidine incorporation in the microtitre plate was measured, while viable T cells ($5 \times 10^6$/ml; $5 \times 10^5$ per well) recovered from bulk cultures were tested for their capacity to suppress the blastogenic response of freshly isolated control NOD T cells to irradiated C57B1/6 stimulators in a 4-day MLR C3H mice, known to have normal suppressor activity, were also included as control animals. Suppressor activity of T cells recovered from bulk cultures was expressed as % suppression:

$$100 \times \frac{\text{mean } \Delta \text{ cpm of the unsuppressed } MLR - \text{mean } \Delta \text{ of the suppressed response}}{\text{mean } cpm \text{ of the unsuppressed response}}$$

The suppressor cell assay yielded most interesting result: whereas control NOD mice could not generate suppressor cells in an autologous MLR, another known immune defect of the NOD mouse (Serreze, D. V. and E. H. Leiter (1988) Defective activation of T suppressor cell function in non-obese diabetic mice. J. Immunol. 140:3801–3807), we observed a complete normalisation of suppressor activity in the 1,25(OH)$_2$D$_3$ treated mice. The existence of suppressor cells was moreover confirmed in cell transfer experiments.

Figure 2:
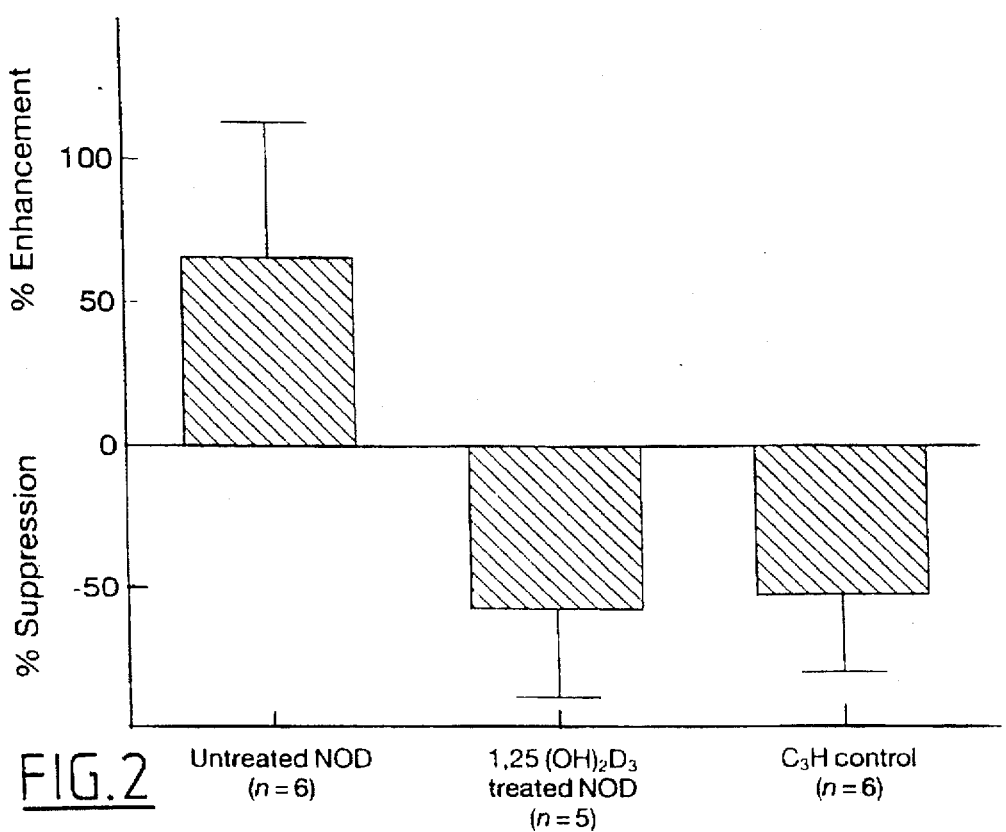
FIG. 2 illustrates the suppression of allogeneic MLR by suppressor cells generated in autologous MLR.

FIG. 2 illustrates the suppression of allogeneic MLR by suppressor cells generated in autologous MLR. When addition of putative suppressor cells did not result in suppression, but in stimulation of the read-out MLR, this was expressed as % enhancement. Mean values ±SD are shown. Number of experiments is shown in parentheses. Statistical analysis was performed by using the Mann Whitney U-test (p<0.05, control NOD vs 1,25(OH)$_{2D3}$ treated NOD).

Cell Transfer Experiments

In this experiments it is shown that the splenocytes of 1,25(OH)$_2$D$_3$-treated animals have a protective effect against the transfer of diabetes.

For diabetes transfer, naïve 6–8 week-old male NOD mice, were irradiated (750 Rad) and, 48 h after irradiation intravenously received $20 \times 10^6$ splenocytes from overtly diabetic NOD mice. In co-transfer experiments, $20 \times 10^6$ splenocytes from animals treated with $1,25(OH)_2D_3$ up to the age of 200 days or from arachis-oil-treated control mice of similar age, were injected i.v. 24 h prior to the transfer of the diabetogenic cells. Mice were tested for glucosuria twice weekly and were considered diabetic following the above-described criteria.

Co-transfer of splenocytes from $1,25(OH)_2D_3$ treated animals significantly delayed and almost completely blocked diabetes transfer into naïve irradiated young male NOD mice (p<0.001 vs controls). Co-transfer with splenocytes from normoglycaemic age-matched (200 days) control NOD mice had no effect.

Figure 3:
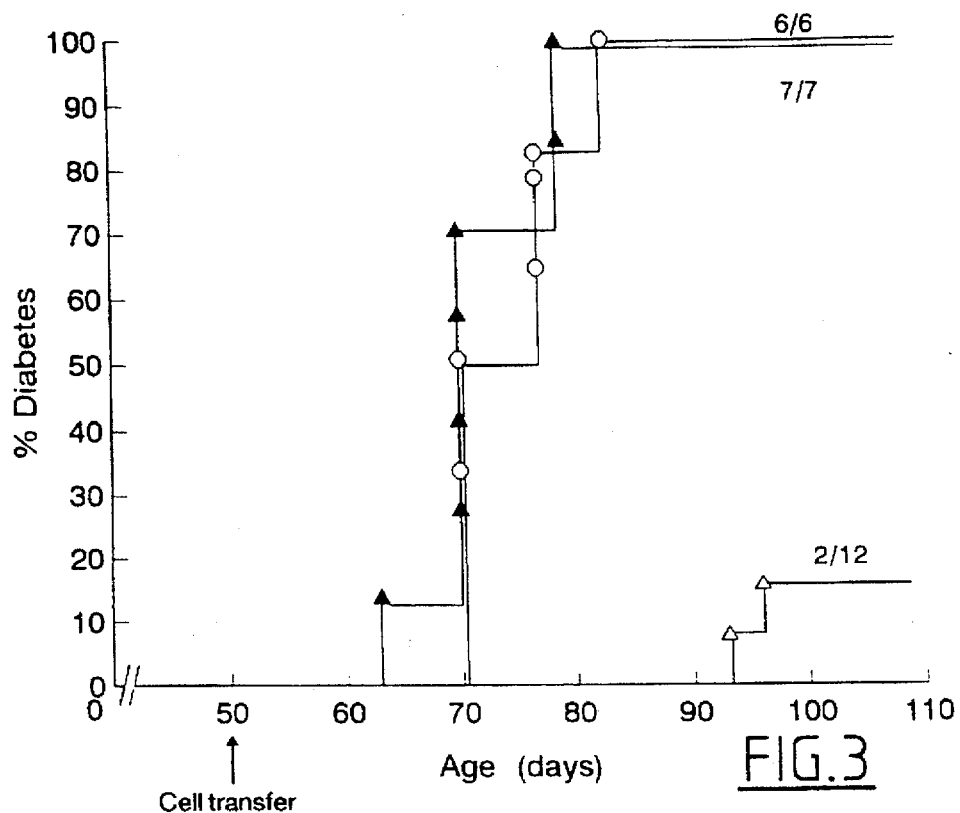
FIG. 3 shows the protective effect of splenocytes from 1,25(OH)$_2$D$_3$-treated NOD mice against diabetes transfer.

FIG. 3 shows the protective effect of splenocytes from $1,25(OH)_2D_3$-treated NOD mice against diabetes transfer. Mice (6–8 week, irradiated 750 Rad) receiving only splenocytes ($20 \times 10^6$ iv) from overtly diabetic NOD mice (▲) developed diabetes within 4 weeks after transfer (n=7). No protective effect was seen when co-transfer was performed with splenocytes ($20 \times 10^6$ i.v.) from normoglycaemic control mice (n=6) (O, NS). Co-transfer with splenocytes from $1,25(OH)_2D_3$ treated mice (n=12), however, protected in the majority of cases against diabetes (Δ, p<0.0001) demonstrating the existence of suppressor cells in these $1,25(OH)_2D_3$.

Statistical Analysis

Data are expressed as means ±SD. Comparison of the incidence of insulitis and diabetes between the two groups was performed using the chi-square test. Significance of differences between immunological data was calculated using the Mann Whitney U-test. Significance was defined at the 0.05 level.

EXAMPLE 2

Primary Treatment of Autoimmune Diabetes by Vitamin D Analogue KH1060 (1α,25(OH)$_2$-20-epi-22-oxa-24,26,27-trishomo vitamin D).

Animals

The NOD, C3H and C57B1/6 mice used in this experiment correspond the annals used in Example 1.

Treatment Regimen $1,25(OH)_2D_3$ (Solvay-Duphar, Weesp, The Netherlands) and KH1060 (Leo Pharmaceuticals, Ballerup, Denmark) were dissolved in arachis oil.

Animals were randomized into four groups: test animals received $1,25(OH)_2D_3$ (n=38) (5 μg/kg), or KH1060 in two different doses ((n=27) (0.4 μg/kg) and (n=27) (0.2 μg/kg.)) in 0.05 ml arachis oil intraperitoneally every other day, while the control group (n=31) received arachis oil (0.05 ml) only. Treatment was started at the age of 21 days an terminated at the age of 200 days or on the day of diabetes diagnosis.

Evaluation of Disease and Insulitis

Mice were weighed weekly and glucosuria was tested three times per week starting from the age of 30 days using Ketodiabur Stix (Boehringer Mannheim, Mannheim, Germany). Glycaemia was measured on a Glucoscot II Glucometer (Menarini, Firenze, Italy). Diabetes was diagnosed in mice having positive glucosuria and glycaemia above 13.8 mmol/l on two consecutive days.

At diabetes diagnosis or at 200 days of age, mice were killed by either inhalation and cervical dislocation (24 h after the final injection). Pancreases were removed, fixed in Bouin's solution. Hematoxylin and eosine stained serial sections were evaluated by two independent investigators.

Figure 4:
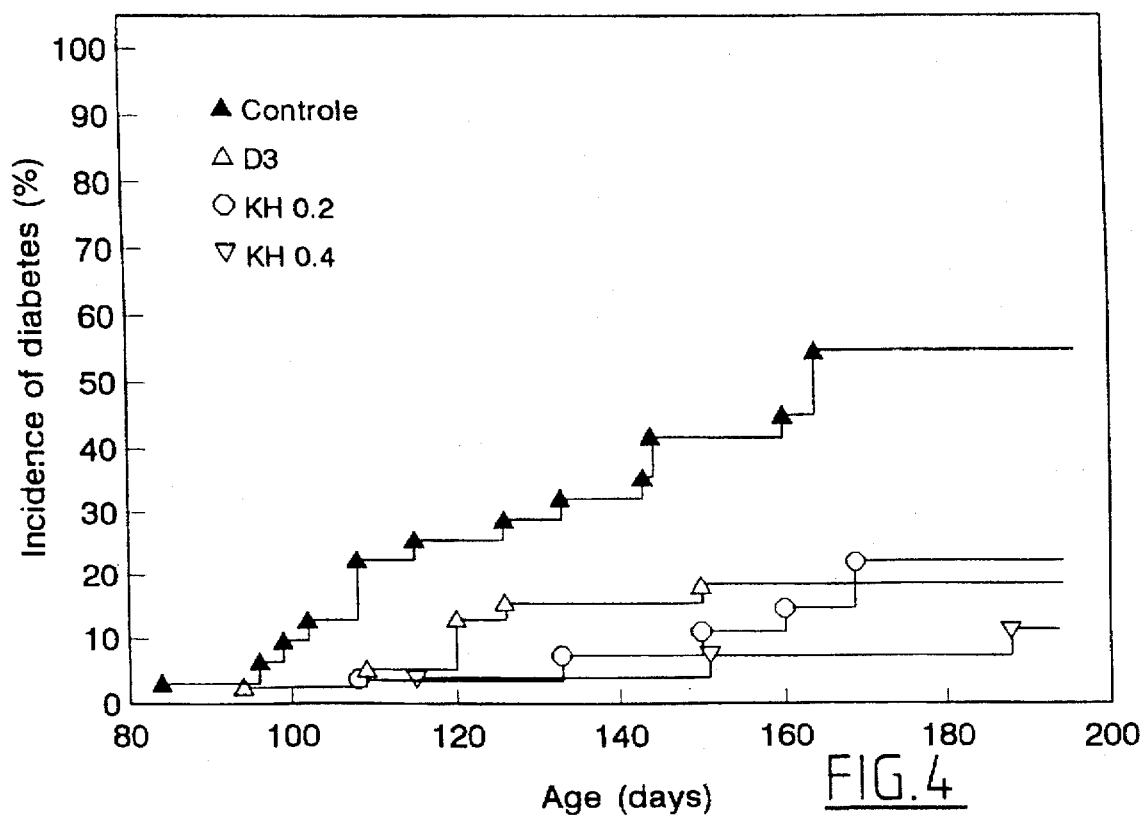
FIG. 4 shows a dose dependent prevention of diabetes that was achieved by the analogue KH1060.

Administration of $1,25(OH)_2D_3$ (5 μg/kg/2d) or either dose of the analogue KH1060 significantly reduced insulitis incidence from 84% (26/31) in the control group to 55% (21/38) in the $1,25(OH)_2D_3$-treated, 44% (12/37) and 48% (13/27) in the low and high dose KH1060-treated groups respectively (p<0.01 in all groups versus controls). As previously demonstrated, diabetes incidence itself could also be significantly reduced by treatment with $1,25(OH)_2D_3$ (18%) versus (55%) in the control group, p<0.005. A dose dependent prevention of diabetes was achieved by the analogue KH1060, since diabetes occured in only 22% and 11% of mice treated with the low and high dose of KH1060 respectively (p<0.001 and p<0.025 versus the control group) (FIG. 4). Severity of insulitis and insulin depletion of the β cells in the islets of Langerhans was also significantly less in all treatment groups.

Suppressor Cell Assay

The capacity to generate suppressor cells in an autologous MLR was tested as described in Serreze & Leiter (1988) J. Immunol. 140(11): 2801–3807 consisting of $5 \times 10^6$/ml test responder T cells, enriched from splenocytes by nylon wool passage, and $^{60}$Co-irradiated (30 Gy) $5 \times 10^6$ /ml test stimulator splenocytes from the same animal were established in 25 cm$^2$ culture flasks kept in upright position. Cells were cultured in the medium used for MLR.

Concurrently, as a read-out system, responder T cells ($5 \times 10^6$/ml) were cocultured with $^{60}$Co-irradiated (30 Gy) $5 \times 10^6$/ml test stimulator splenocytesin flat-bottomed 96-well microtiter plates in a final volume of 0.2 ml.

On day 6 [methyl-$^3$H]thymidine incorporation in the microtiter wells was measured while viable cells ($5 \times 10^6$/ml; $5 \times 10^5$/well) recovered from the bulk cultures were tested for their capacity to suppress the blastogenic response of freshly isolated control NOD T cells to irradiated C57B1/6 stimulators in a 4 day MLR.

C3H mice, known to have a normal capacity to generate suppressor cells, were also included as controle animals. Suppressor activity was determined as described in Example 1.

Figure 5:
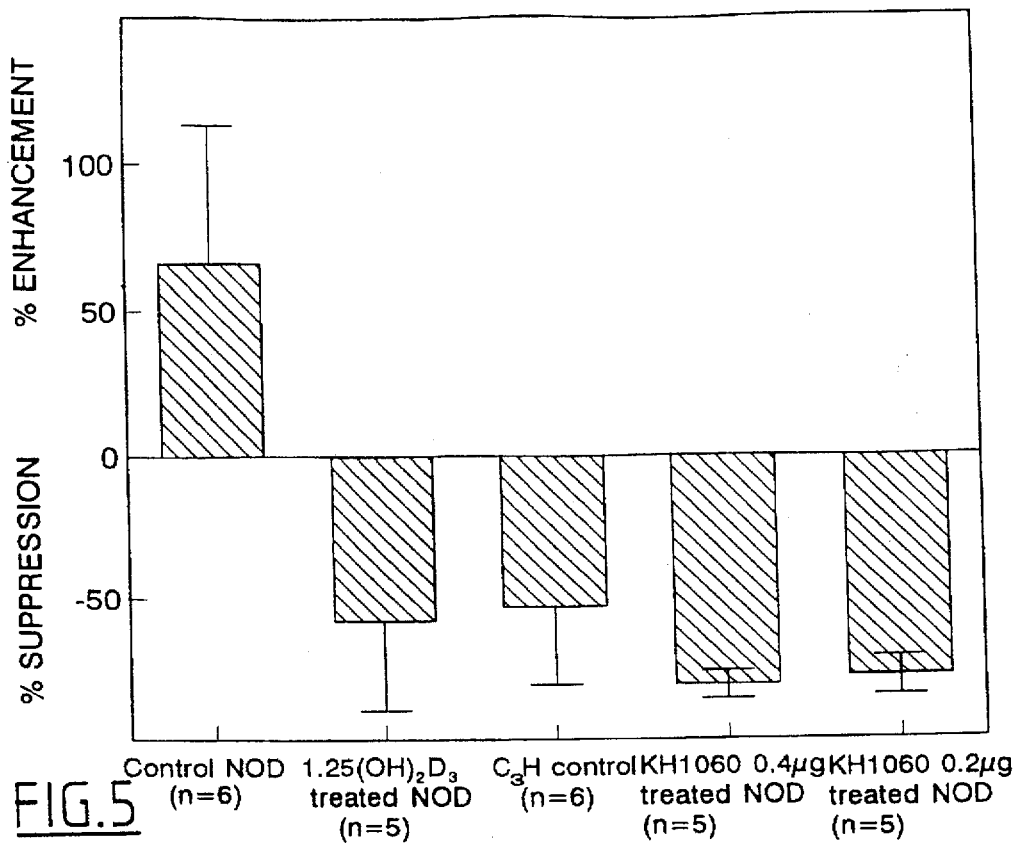
FIG. 5 shows to cell proliferation in the read-out allogeneic MLR.

Suppression of a read-out allogeneic MLR gives an indication of the generation of suppressor cells in an autologous MLR. As is typical for NOD mice, no suppressor cells could be raised in control mice. Mice from all three treatment groups however, showed a restoration of this treatment groups however, showed a restoration of this potential to generate suppressor cells in vitro as compared to control animals. Indeed, T cell proliferation in the read-out allogeneic MLR could almost totally a suppressed in all treatment groups (FIG. 5). The presence of suppressor cells was confirmed in vivo in transfer experiments.

Cell Transfer Experiments

Figure 6:
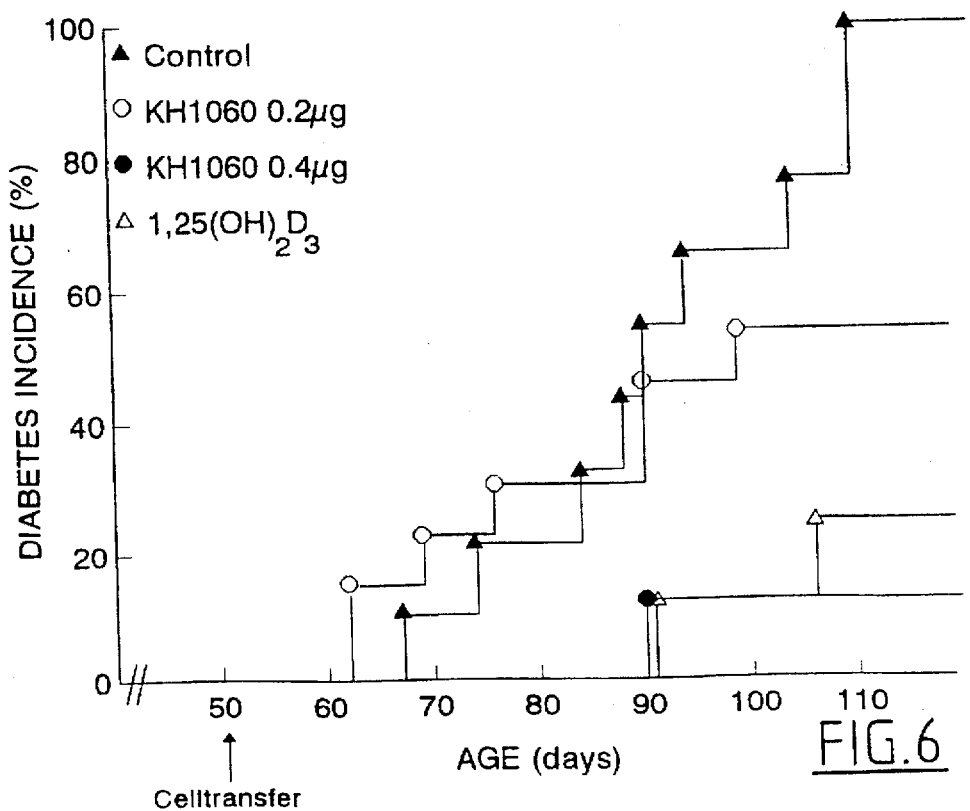
FIG. 6 shows how splenocytes from mice treated with 1,25 (OH)$_2$D$_3$ were clearly able to prevent diabetes transfer by splenocytes taken from overtly diabetic mice into young irradiated naieve NOD mice.

Splenocytes from mice treated with $1,25 (OH)_2D_3$ were clearly able to prevent diabetes transfer by splenocytes taken from overtly diabetic mice into young irradiated naieve NOD mice (FIG. 6). These suppressor cells could also be demonstrated in NOD mice treated with KH1060 at 0.4 μg/kg/2d. Splenocytes taken from protected mice treated with KH1060 at 0.2 μg/kg/2d could however not prevent diabetes transfer, indicating absence or relatively low numbers of active suppressor cells in the spleens of these animals.

In conclusion, in this example it has been demonstrated that the new structural analogue of $1,25(OH)_2D_3$, KH1060, prevents insulitis and diabetes in the spontaneously diabetic NOD mouse. The disease prevention could be achieved without any significant effect on calcium and bone metabolism (Table 1) and is probably, in analogy to $1,25(OH)_2D_3$, mediated through the restoration of the ability to generate suppressor cells in the autoimmunity prone NOD mouse. It is therefore believed that vitamin D analogues are a new class of immunomodulatory agents, that either alone or in combination with other drugs, could find therapeutical applications in the prevention of autoimmune diseases, such as type I diabetes.

TABLE 1

Effects of $1,25(OH)_2D_3$ and KU 1060 on calcium metabolism

| | Calcium (mg/dl) | Osteocalcin (µ/l) | Bone calcium (mg/tibia) |
|---|---|---|---|
| Control (n = 31) | 9.5 ± 0.6 | 82 ± 18 | 6.4 ± 0.5 (n = 17) |
| $1,25(OH)_2D_3$ (n = 38) | 9.6 ± 0.5 | 133 ± 16 | 4.1 ± 0.7 (n = 9) |
| | N.S. | $p < 0.00001$ | $p < 0.00001$ |
| KH1060 0.2 µg/kg (n = 27) | 9.6 ± 0.4 | 78 ± 17 | 6.8 ± 0.7 (n = 16) |
| | N.S. | N.S. | N.S. |
| KH1060 0.4 µg/kg (n = 27) | 10.8 ± 0.8 | 74 ± 13 | 6.5 ± 0.8 (n = 15) |
| | $p < 0.0001$ | N.S. | N.S. |

EXAMPLE 3

Secondary Treatment of Autoimmune Diabetes by a Vit. D Analogue, KH1060

The aim of this example was to design new immunosuppressive/immunomodulatory strategies that are first of all able to prevent autoimmune disease recurrence and secondly eventually reinduce tolerance after islet transplantation. Using the model of syngeneic islet transplantation in the spontaneously diabetic NOD mouse allowed for focussing on recurrence, since allograft rejection does not occur syngeneic combinations.

The capacity of a new structural analogue of 1,25(OH)$_2$D$_3$, KH1060, to prevent autoimmune recurrence alone and in combination with cyclosporin A was tested. The choice of an analogue of $1,25(OH)_2D_3$ came from the observations made in the primary prevention trial: if $1,25(OH)_2D_3$ prevent type I diabetes in MOD mice by restoring the balance in the immune system, a more potent analogue of this drug might well be able to reinstall tolerance after islet transplantation.

The use of the combination with Cyclosporin A came from observation made in vitro: $1,25(OH)_2D_3$ acts additionally with Cyclosporin A in the suppression of T cell proliferation and cytokine production.

Therefore, in this example the capacity of the structural analogue of $1,25(OH)_2D_3$, KH1060 ($\alpha,25(OH)_2$-20-epi 22-oxa-24,26,27-trishomo vitamin D) in the prevention of autoimmune disease recurrence after isle transplantation both in monotherapy an in combination with low doses of Cyclosporin A was evaluated.

Islet Transplantation

Syngeneic islet transplantations were performed by the technique derived from the previously described technique in the rat (Kuttler, B., Mathieu, C., Waer, M., Hahn, H. J. and Bouillon, R. (1993) Lack of disease recurrence in diabetic BB/Pfd rats after syngeneic islet transplantation. Autoimmunity 15:107–112). Some differences exist however. Briefly, pancreases were removed aseptically from 14 to 21 days old donor NOD mice and the exocrine tissue was digested by fractionated collagenase digestion in HBSS. Islets were isolated form the exocrine digest via direct handpicking under a stereomicroscope.

Recipient animals were anaestethised with ether an the target organ was approached via a lumbotomy. Fresh islets, suspended in ice cold RPMI 1640 supplemented with 10% FCS were transplanted under the left kidney capsule of the recipient mouse (500 per recipient). Animals recovered swiftly and normoglycemia was reached in most animals within 24 hours.

Control mice were treated with the treatment vehicle (arachis oil) only, while 3 different groups of KH1060-treated mice were made: KH 0.5 µg/kg/d, KH 0.5 µg/kg/d, KH 0.5 µg/kg/2d and KH 1 µg/kg/2d. Also different doses of Cyclosporin A were used: CyA 7.5 mg/kg/d and CyA 15 mg/kg/d. Finally a combination of the subtherapeutical doses of both drugs were made KH 0.5 µg/kg/2d+CyA 7.5 mg/kg/d. All drugs were administered intraperitoneally and treatments were initiated the day before transplantation. Table 2 below represents schematically the different groups and their treatment.

TABLE 2

| Day of transplantation | | Day of recurrence or day 60 | Day 90 |
|---|---|---|---|
| ↓ | | ↓ | |
| day-1 | ————————————————————————— | | |
| Control (Arachis oil) | ↑↑↑↑↑↑↑↑↑↑↑↑↑↑↑↑↑↑↑↑↑↑↑↑↑↑↑↑↑ ———— | | |
| KH 0.5 µg/kg/2d | ↑ ↑ ↑ ↑ ↑ ↑ ↑ ↑ ↑ ↑ ↑ ↑ ↑ ↑ ↑ ———— | | |
| KH 0.5 µg/kg/d | ↑↑↑↑↑↑↑↑↑↑↑↑↑↑↑↑↑↑↑↑↑↑↑↑↑↑↑↑↑ ———— | | |
| KH 1 µg/kg/2d | ↑ ↑ ↑ ↑ ↑ ↑ ↑ ↑ ↑ ↑ ↑ ↑ ↑ ↑ ↑ ———— | | |
| CyA 7.5 mg/kg/d | ↑↑↑↑↑↑↑↑↑↑↑↑↑↑↑↑↑↑↑↑↑↑↑↑↑↑↑↑↑ ———— | | |
| CyA 15 mg/kg/d | ↑↑↑↑↑↑↑↑↑↑↑↑↑↑↑↑↑↑↑↑↑↑↑↑↑↑↑↑↑ ———— | | |
| KH 0.5 µg/kg/2d + | ↑ ↑ ↑ ↑ ↑ ↑ ↑ ↑ ↑ ↑ ↑ ↑ ↑ ↑ ↑ ———— | | |
| CyA 7.5 mg/kg/d | ↑↑↑↑↑↑↑↑↑↑↑↑↑↑↑↑↑↑↑↑↑↑↑↑↑↑↑↑↑ ———— | | |

Post transplantation all animals were weighed and tested for recurrence of diabetes (through detection of glucosuria and hypercalcemia) every other day. Animals were considered diabetic when having glucosuria and hyperglycemia (blood glucose>12 mmol) on 2 consecutive days. Upon disease recurrence or 30 days after stopping the treatment in non-recurring mice, animals were bled by heart puncture and killed by cervical dislocation. Serum calcium levels, osteocalcin and bone calcium were determined as parameters of calcium metabolism. Grafts and pancreases were taken for insulin content determination.

Prevention of Disease Recurrence

Control animals showed disease recurrence in 100% of the cases (8/8) within 2 weeks after transplantation (Table 3). Treatment with high doses of cyclosporin A (15 mg/kg) prevented recurrence under treatment in 50% of mice (3/6), but only one of the protected animals maintained a functioning graft more than 30 days after interruption of the therapy.

The structural analogue of $1,25(OH)_2D_3$, KH1060, also succeeded in significantly prolonging the islet survival (MST 5 days) when the highest dose (1 µg/kg/2d) was used. In this group 3 of 8 animals showed an islet graft survival of more than 60 days, with however again recurrence of disease after stopping the therapy.

TABLE 3

| | Number of animals | Survival of islets (d) | MST (d) | p |
|---|---|---|---|---|
| Control | 8 | 5,7,7,8, 8,9,10,13 | 8 | — |
| KH 0.5 µg/kg/2d | 5 | 4,8.11, 19,19 | 12 | N.S. |
| KH 0.5 µg/kg/d | 5 | 10,11,13, 15,18 | 13 | p < 0.01 |
| KH 1 µg/kg/2d | 8 | 20,39,41, 56,60,63, 70,70 | 55 | p < 0.0001 |
| CSA 7.5 mg/kg/d | 8 | 4,5,7,8, 13,14,37, 42 | 16 | N.S. |
| CSA 2.5 mg/kg/d | 6 | 22,45,55, 67,69,>90 | >58 | p < 0.0001 |
| KH 0.5 µg/kg/2d + CSA 7.5 mg/kg/d | 7 | 7,33,35, >90,>90, >90,>90 | >62 | p <0.0001 |

All mice were spontaneously diabetic NOD mice transplanted with 500 NOD islets under the left kidney capsule. Statistical analysis was performed using the Students t-test for unpaired data. P values in comparison to the control group were shown.

When mice were treated with subtherapeutical doses of both drugs combined (KH1060 0.5 µg/kg/2+CyA 7.5 mg/kg/d) which by themselves could only slightly prolong islet survival, 4 of 7 mice maintained a functioning graft for 60 days and more importantly, these animals did not show recurrence for at least 30 days after stopping the treatment.

Insulin content determinations of the graft and native pancreas of the recipient clearly demonstrated that normoglycemia was the result of graft survival and not of recovery of the β cells of the recipients own pancreas: insulin content in pancreases of recurring and non recurring mice was comparable and showed no regeneration of the original β cells (0.0125±0.012 pmol/mg in recurring versus 0.008±0.004 pmol/mg in non recurring mice, NS) while the insulin content in the grafts showed a clear difference between recurring and non recurring mice (45±27 pmol/graft in recurring versus 1285±106 pmol/graft in non recurring mice, p<0.00001).

In this example it was demonstrated that a new structural analogue of $1,25(OH)_2D_3$, KH1060, given in high (1 µg/kg/2d) doses can delay autoimmune disease recurrence after syngeneic islet transplantation in NOD mice. These doses are however toxic, partly due to hypercalcemia. The combination of non toxic subtherpeutical doses of KH1060 (0.5 µg/kg/2d) with subtherapeutical doses of Cyclosporin A synergistically prevented recurrence of autoimmune diabetes and reinstalled tolerance after syngeneic islet transplantation in NOD mice.

Recurrence of autoimmune diabetes remains a problem in islet transplantation in type I diabetes. Indeed, to maintain the function of islet allografts in type I diabetic patients, higher doses of immunosuppressants are needed than in surgically induced diabetes as not only allograft rejection but also autoimmune memory has to be suppressed.

In the above it was demonstrated that the highest tolerable dose of KH1060 (1 µg/kg/2d) significantly prolonged the survival of syngeneic islets in NOD mice, to the same extent as the highest tolerable dose of Cyclosporin A.

In vitro an additive effect between $1,25(OH)_2D_3$ and the conventional immunosuppressants (Cyclosporin A, FK 506 or rapamycin) on T cell proliferation and cytokine production (IL-2, TNFα and IFNγ) in human MLR has been demonstrated (Mathieu, C., Bouillon, R., Rutgeerts, O., Vandeputte, M. and Waer, M. A potential role of 1,25(OH)$_2$vitamin D$_3$ as a dose reducing agent for cyclosporin A and FK506. Transpl. Proceed., in press). By adding subtherapeutical concentrations of $1,25(OH)_2D_3$, the IC$_{50}$ of Cyclosporin A, FK 506 and rapamycin was reduced 10 fold, 5 fold and 5 fold, respectively. A similar additive and even synergistic effect was observed in vivo between subtherapeutical, non-toxic doses of KH1060 and subtherapeutical doses of Cyclosporin A, as illustrated in this example. A combination of these drugs not only preveneted disease recurrence during therapy, but probably succeeded in breaking the autoimmune memory in 57% of animals, since no recurrence was observed even up to 30 days after discontinuation of all treatment in these mice.

In conclusion, a new structural analogue of $1,25(OH)_2D_3$, KH1060, prolongs survival of syngeneic islet grafts in spontaneously diabetic NOD mice, both alone and more importantly, in synergy with Cyclosporin A. We therefore propose a possible role for KH1060 or other new preferably non calcemic analogues of $1,25(OH_2D_3$ as dose reducing agents for classical immunosuppressive drugs such as Cyclosporin A, FK 506 an rapamycin. In this manner, the structural analogues of $1,25(OH)_2D_3$ could well be the future corticosteroid replacing drugs thus avoiding many side effects in organ transplantation and other diseases requiring immunosuppression, especially considering the potential of $1,25(OH)_2D_3$ and its analogues to induce tolerance.

We claim:

1. A method for modulating the immune system of a subject comprising administrating an amount in a range of 0.1 ug to 1 mg per kilogram body-weight of said subject of a first compound based on the formula

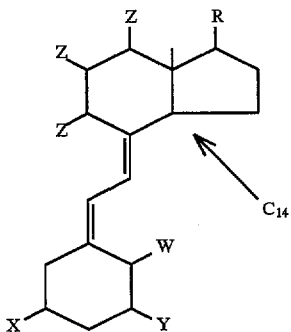

wherin x is $H_2$ or $H(OH)$; Y is $H(OH)$ or $H(F)$; Z is $H_2$ or $H$ (alkyl) ($C_1$–$C_4$); W is $H_2$,=$CH_2$ or $H(CH_3)$ and R is

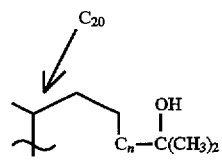

wherein one or more carbon atoms may be replaced by O or S and wherein n<3, or alkyl-, aryl-, alkenyl-, alkynyl-, fluoro-, thio-, cycloalkyl-, epoxy-, hydroxyl- or keto-containing derivatives thereof; and wherein said amount is effective to modulate the immune system in an animal or patient to which said amount is administered.

2. The method according to claim 1 wherein said amount of said first compound is effective to upregulate the suppressor arm of the immune system in an animal or patient to which said amount is administered.

3. The method according to claim 1 wherein said amount of said first compound provides to said animal or human at least twice the physiological does of said compound and said amount is effective to modulate the immune system so as to effect treatment of autoimmune diabetes.

4. The method according to claim 1 wherein said amount of said first compound provides to said animal or human at least five times the physiological dose of said compound and said amount is effective to modulate the immune system so as to effect treatment of autoimmune diabetes.

5. The method according to claim 1 wherein said amount of said first compound provides to said animal or human between 10 to 100 times the physiological dose of said compound and said amount is effective to modulate the immune system so as to effect treatment of autoimmune diabetes.

6. The method according to claim 1 wherein said first compound is coadministered with a second compound having immune system modulation activity so as to effect treatment of autoimmune diabetes.

7. The method according to claim 6 wherein said second compound is Cyclosporin A.

8. The method according to claim 6 wherein said first compound and said Cyclosporin A are each administered to said animal or human in amounts smaller than the applicable dose for either said first compound or said Cyclosporin A administered alone, and said combined amounts are effective to modulate the immune system so as to effect treatment of autoimmune diabetes.

9. The method according to claim 1 wherein said first compound is administered as a pharmaceutical formulation containing at least one pharmaceutically acceptable excipient and said amount of said first compound.

10. The method according to claim 9 wherein said pharmaceutical formation is selected from the group consisting of powders, suspensions, solutions, emulsions, capsules or tablets for enteral or parenteral administration.

11. A pharmaceutical composition in unit dosage form effective to modulate the immune system, comprising at least one pharmaceutically acceptable excipient and an amount of a first compound based on the formula

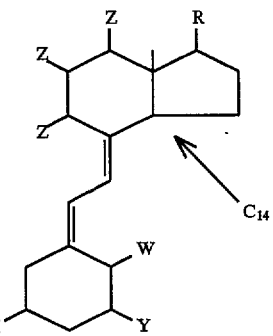

wherein x if $H_2$ or $H(OH)$; Y is $H(OH)$ or $H(F)$; Z is $H_2$ or $H$ (alkyl) ($C_1$–$C_4$); W is $H_2$,=$CH_2$ or $H(CH_3)$ and R is

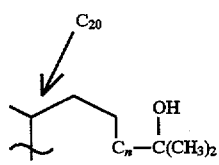

wherein one or more carbon atoms may be replaced by O or S and wherein n<3 or alkyl-, aryl-, alkenyl-, alkynyl-, fluoro-, thio-, cycloalkyl-, epoxy-, hydroxyl- or keto-containing derivatives thereof; and wherein said amount is effective to modulate the immune system in an animal or patient to which said amount is administered.

12. The pharmaceutical composition according to claim 11 wherein said composition is selected from the group consisting of powder, supensions, solutions, emulsions, capsules or tablets for enteral or parenteral administration.

13. The pharmaceutical composition according to claim 11 wherein said unit dosage is higher than the physiological dose of said first compound.

14. The pharmaceutical composition according to claim 13 wherein said unit dosage is at least twice the physiological dose.

15. The pharmaceutical composition according to claim 14 wherein said unit dosage is at least five times the physiological dose.

16. The pharmaceutical composition according to claim 15 wherein said unit dosage is at least 10 times the physiological dose.

17. The pharmaceutical composition according to claim 11 wherein said unit dosage is between 10 and 100 times as high as the physiological dose of said first compound.

18. The pharmaceutical composition according to claim 11 further containing an amount of a second compound having immune system modulating activity so as to effect treatment of autoimmune diabetes.

19. The pharmaceutical composition according to claim 18 wherein said second compound is Cyclosporin A.

* * * * *

UNITED STATES PATENT AND TRADEMARK OFFICE
CERTIFICATE OF CORRECTION

PATENT NO. : 5,665,387
DATED : September 9, 1997
INVENTOR(S) : Chantal Mathieu, Mark Waer and Roger Bouillon It is certified that error appears in the above-identified patent and that said Letters Patent is hereby corrected as shown below:

Column 1 Line 16 "Eisenbirth" should read --Eisenbarth--.

Column 1 Line 34 "new cells" should read --new β cells--.

Column 1 Line 34 "he memory cells" should read --the memory cells--.

Column 1 Line 35 "of the cells" should read --of the β cells--.

Column 1 Line 67 "as animal" should read --as an animal--.

Column 2 Line 2 after "diabetes" insert --is an--.

Column 2 Line 2 "can he" should read --can be--.

Column 2 Line 3 "by environmental" should read --by unknown environmental--.

Column 2 Line 3 "environmental favors" should read --environmental factors--.

Column 2 Line 3 "predispose" should read --predisposed--.

Column 2 Lines 4-5 "reactor/suppressor" should read --regulator/suppressor--.

Column 2 Line 6 "producing cells" should read --producing β cells--.

Column 2 Line 7 "effective disease" should read --effective in disease--.

Column 2 Line 11 "a" should read --arm--.

Column 2 Line 11 "of the system" should read --of the immune system--.

UNITED STATES PATENT AND TRADEMARK OFFICE
CERTIFICATE OF CORRECTION

PATENT NO. : 5,665,387
DATED : September 9, 1997
INVENTOR(S) : Chantal Mathieu, Mark Waer and Roger Bouillon It is certified that error appears in the above-identified patent and that said Letters Patent is hereby corrected as shown below:

Column 2 Line 12 "impairing global" should read --impairing the global--.

Column 2 Line 25 "obstacle preclinical" should read --obstacle to preclinical--.

Column 2 Line 26 after "$D_3$" insert --is--.

Column 2 Line 33 "Of 1,25" should read --of 1,25--.

Column 2 Line 42 after "amount" insert --effective--.

Column 3 Line 10 "n(3" should read --n<3--.

Column 3 Line 23 "yne-26,27$F_6$,-$D_3$" should read --yne-26,27-$F_6$-$D_3$--.

Column 3 Line 26 "22oxa" should read --22-oxa--.

Column 3 Line 26 "1α25" should read --1α,25--.

Column 3 Line 27 after "(OH)$_2D_3$," and before "1α-F" insert --20-epi-24-homo-1α,25-(OH)$_2D_3$, 20-epi-22-oxa-24,26a,27a-trihomo- 1α,25-(OH)$_2D_3$,--.

Column 3 Line 28 "α-F" should read --1α-F--.

Column 3 Line 29 "27,-$d_6$" should read --27-$d_6$--.

Column 3 Lines 30-31 "dehydro-$F_3$" should read --dehydro-$D_3$--.

Column 3 Line 31 "(OH)$_2$,22,23" should read --(OH)$_2$-22,23--.

Column 3 Line 33 "22,23diene" should read --22,23-diene--.

Column 3 Line 35 "1α(OH)" should read --1α-(OH)--.

Page 2 of 6

UNITED STATES PATENT AND TRADEMARK OFFICE
CERTIFICATE OF CORRECTION

PATENT NO. : 5,665,387
DATED : September 9, 1997
INVENTOR(S) : Chantal Mathieu, Mark Waer and Roger Bouillon It is certified that error appears in the above-identified patent and that said Letters Patent is hereby corrected as shown below:

Column 3 Line 35 "$(OH)_2-(OH)_2$" should read --$(OH)_2$--.

Column 3 Line 38 "27, -$d_6$" should read --27-$d_6$--.

Column 3 Line 39 "1α,25$(OH)_2$" should read --1α,25-$(OH)_2$--.

Column 3 Line 44 "26homo" should read --26-homo--.

Column 3 Line 46 "$(OH)_2$-24$F_2D_3$" should read --$(OH)_2$-24-$F_2$-$D_3$--.

Column 3 Line 49 "27diethyl" should read --27-diethyl--.

Column 3 Line 54 "$D_3$1α,25" should read --$D_3$, 1α,25--.

Column 3 Line 56 "25$(OH)_2$" (1st occurrence) should read --25-$(OH)_2$--.

Column 3 Line 57 "26,27dihomo" should read --26,27-dihomo--.

Column 3 Line 58 "24a,24-dihomo" should read --24a,24b-dihomo--.

Column 3 Line 62 "isolated cells β" should read --isolated β cells--.

Column 4 Line 4 "the invention" should read --The invention--.

Column 4 Line 12 "usually use" should read --usually used--.

Column 4 Line 21 "a method or" should read --a method for--.

Column 4 Line 22 "on β" should read --or β--.

Column 4 Line 40 "may he such" should read --may be such--.

Column 5 Line 20 "were purchase" should read --were purchased--.

Column 5 Line 27 "Hoffman Roche" should read --Hoffman-La Roche--.

UNITED STATES PATENT AND TRADEMARK OFFICE
CERTIFICATE OF CORRECTION

PATENT NO. : 5,665,387
DATED : September 9, 1997
INVENTOR(S) : Chantal Mathieu, Mark Waer and Roger Bouillon It is certified that error appears in the above-identified patent and that said Letters Patent is hereby corrected as shown below:

Column 5 Line 27 "as" should read --was--.

Column 5 Line 30 "receive" should read --received--.

Column 5 Line 48 "cosine" should read --eosine--.

Column 5 Line 57 "2=per-islet" should read --2=peri-islet--.

Column 6 Line 12 "(n-36)" should read --(n=36)--.

Column 6 Line 46 "yielded most" should read --yielded a most--.

Column 6 Line 62 "$1,25(OH)_{2D3}$" should read --$1,25(OH)_2D_3$--.

Column 7 Line 43 "correspond the" should read --correspond to the--.

Column 7 Line 43 "annals" should read --animals--.

Column 7 Line 50 "kg.))" should read --kg))--.

Column 7 Line 53 "an terminated" should read --and terminated--.

Column 8 Line 19 "2801-3807" should read --3801-3807--.

Column 8 Line 19 after "3807" insert --. Briefly, bulk cultures--.

Column 8 Line 27 "$5x10^6//ml$" should read --$5x10^6/ml$--.

Column 8 Line 43 after "restoration of this" delete --treatment groups however, showed a restoration of this--.

Column 8 Line 57 before "could" delete --and--.

UNITED STATES PATENT AND TRADEMARK OFFICE
CERTIFICATE OF CORRECTION

PATENT NO. : 5,665,387
DATED : September 9, 1997
INVENTOR(S) : Chantal Mathieu, Mark Waer and Roger Bouillon It is certified that error appears in the above-identified patent and that said Letters Patent is hereby corrected as shown below:

Column 9 Line 10, Table 1 header, "KU 1060" should read --KH 1060--.

Column 9 Table 1, Column heading "Osteocalcin ($\mu$/l)" should read --Osteocalcin ($\mu$g/l)--.

Column 9 Table 1, under Column headed "Bone Calcium, row 5 of 11, "p<0.00001" should read --p<0.0001--.

Column 9 Line 35 "occur syngeneic" should read --occur in syngeneic--.

Column 9 Lines 40-41 "prevent" should read --prevents--.

Column 9 Line 41 "MOD mice" should read --NOD mice--.

Column 10 Line 5 "from observation made" should read --from observations made--.

Column 10 Line 9 "($\alpha$,25(OH)" should read --(1$\alpha$,25(OH)--.

Column 10 Line 11 "isle" should read --islet--.

Column 10 Line 12 "an in" should read --and in--.

Column 10 Line 34 after "made: KH 0.5$\mu$g/kg/d," delete second occurrence of --KH 0.5$\mu$g/kg/d--.

Column 11 Line 5 "mmol" should read --mmol/l--.

Column 11 Line 22 "(MST 5 days)" should read --(MST 55 days)--.

Column 11 Table 3, first column, row 6: "CSA 2.5" should read --CSA 15--.

Column 11 Line 53 "2+CyA" should read --2d+CyA--.

UNITED STATES PATENT AND TRADEMARK OFFICE
CERTIFICATE OF CORRECTION

PATENT NO. : 5,665,387
DATED : September 9, 1997
INVENTOR(S) : Chantal Mathieu, Mark Waer and Roger Bouillon It is certified that error appears in the above-identified patent and that said Letters Patent is hereby corrected as shown below:

Column 12 Line 29 "TNFαand" should read --TNFα and--.

Column 12 Line 55 "an rapamycin" should read --and rapamycin--.

Claim 1 Column 13 Line 15 "wherin" should read --wherein--.

Claim 5 Column 13 Line 47 "between 10 to 100" should read --between 10 and 100--.

Claim 10 Column 14 Line 2 "formation" should read --formulation--.

Claim 11 Column 14 Line 24 "wherein x if $H_2$" should read --wherein x is $H_2$--.

Claim 12 Column 14 Line 43 "powder" should read --powders--.

Signed and Sealed this

Seventeenth Day of February, 1998

Attest:

BRUCE LEHMAN

*Attesting Officer*     *Commissioner of Patents and Trademarks*